US012648902B2

(12) United States Patent (10) Patent No.: US 12,648,902 B2
Jeon et al. (45) Date of Patent: Jun. 9, 2026

(54) FERMENTED APPLE COMPOSITION

(71) Applicant: CJ CHEILJEDANG CORPORATION, Seoul (KR)

(72) Inventors: Kyung Chan Jeon, Seoul (KR); Hee Kyoung Jung, Seoul (KR); Sunhee Kim, Seoul (KR); Yeeun Park, Seoul (KR); Eunyong Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 18/275,364

(22) PCT Filed: Dec. 5, 2022

(86) PCT No.: PCT/KR2022/019571
§ 371 (c)(1),
(2) Date: Aug. 1, 2023

(87) PCT Pub. No.: WO2024/025050
PCT Pub. Date: Feb. 1, 2024

(65) Prior Publication Data
US 2025/0144004 A1 May 8, 2025

(30) Foreign Application Priority Data
Jul. 29, 2022 (KR) ........................ 10-2022-0094864

(51) Int. Cl.
*A61K 36/00* (2006.01)
*A61K 8/9789* (2017.01)
*A61K 36/73* (2006.01)
*A61P 17/16* (2006.01)
*A61Q 19/08* (2006.01)
*C12J 1/00* (2006.01)

(52) U.S. Cl.
CPC ............ *A61K 8/9789* (2017.08); *A61K 36/73* (2013.01); *A61P 17/16* (2018.01); *A61Q 19/08* (2013.01); *C12J 1/00* (2013.01); *A61K 2236/19* (2013.01); *A61K 2800/782* (2013.01); *A61K 2800/85* (2013.01)

(58) Field of Classification Search
CPC .................................................. A61K 2236/19
See application file for complete search history.

(56) References Cited

U.S. PATENT DOCUMENTS

2019/0142045 A1* 5/2019 Baek .......................... C12J 1/04
426/52

FOREIGN PATENT DOCUMENTS

| | | | |
|---|---|---|---|
| JP | 2013-180958 A | 9/2013 | |
| KR | 10-0911108 B1 | 8/2009 | |
| KR | 10-1227366 B1 | 1/2013 | |
| KR | 10-2014-0052127 A | 5/2014 | |
| KR | 10-2016-0044642 A | 4/2016 | |
| KR | 10-2020-0038724 A | 4/2020 | |
| KR | 20200038724 A | * 4/2020 | ........... A23L 33/105 |

OTHER PUBLICATIONS

Extended European Search Report issued May 6, 2024 for European Patent Application No. 22908856.2.
Liminjer et al., "Current and Research Progress in Apple vinegar", Gansu Agr. Sci. and Techn., No. 7, Jul. 2018, pp. 83-87.
Office Action issued in corresponding Chinese Patent Application No. 202280011094.5, dated Jun. 19, 2025.
Office Action issued in corresponding Japanese Patent Application No. 2023-542803, dated Sep. 3, 2024.
Office Action issued in corresponding Japanese Patent Application No. 2023-542803, dated Mar. 18, 2025.
Zhang et al., "Polyphenols in fermented apple juice: Beneficial effects on human health," Journal of Functional Foods, 76, 104294: 1-16 (2021).
Lee et al., "Photo-aging regulation effects of newly bred Green ball apple," Journal of Applied Biological Chemistry, 63 (1): 75-82 (2020).
International Search Report issued in corresponding International Patent Application No. PCT/KR2022/019571 dated Apr. 24, 2023.

* cited by examiner

*Primary Examiner* — Qiuwen Mi
(74) *Attorney, Agent, or Firm* — Morgan, Lewis & Bockius LLP

(57) ABSTRACT
Provided are a fermented apple composition having an effect of reducing or inhibiting UV-induced collagenase expression, and use thereof in the skin improvement and in the prevention or inhibition of skin photoaging.

14 Claims, 1 Drawing Sheet

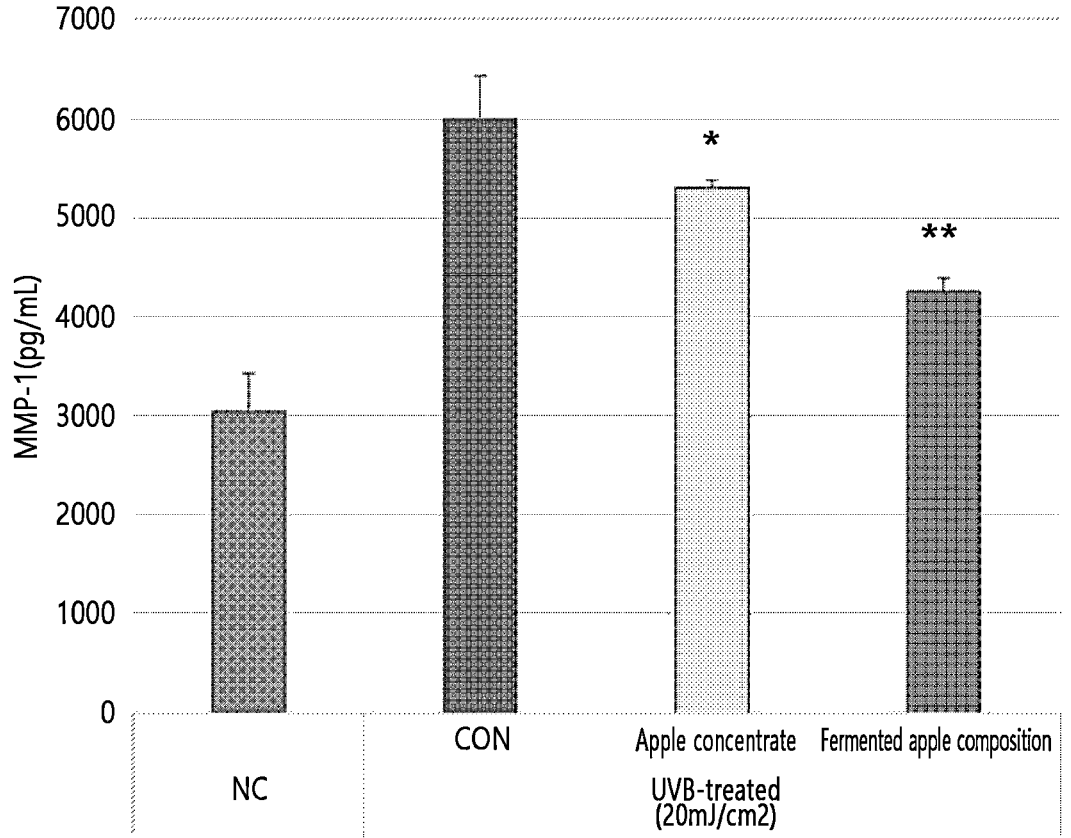

FERMENTED APPLE COMPOSITION

TECHNICAL FIELD

The present disclosure relates to a fermented apple composition, and use thereof in the skin improvement and in the prevention or inhibition of skin photoaging.

BACKGROUND ART

Recently, there has been increasing interest in delaying or relaxing skin aging in the context of skin beauty. In particular, as interest in photoaging caused by UV exposure, in addition to natural aging, has rapidly increased, a number of products have been developed to prevent or suppress photoaging.

Photoaging is a phenomenon in which collagens in the dermal layer are degraded by UV-generated reactive oxygen species (ROS) in skin cells. When ROS generated by UV stimulation penetrates into cells and induces expression of matrix metalloproteinase-1 (MMP-1), which is an enzyme that degrades collagen, the overexpressed MMP-1 degrades collagen in the dermal layer of the skin, resulting in loss of skin elasticity and aging. Therefore, in order to prevent or inhibit photoaging, it is necessary to develop a substance capable of effectively inhibiting MMP-1 expression.

On the other hand, apples are fruits of the apple tree, which is a perennial plant belonging to the genus Malus, the family Rosaceae, and they have a high content of sugar, vitamin A, vitamin C, and inorganic salts. Vitamin C, which is contained in large amounts in apples, has an excellent effect of regenerating damaged skin cells by strengthening the bond between keratin and collagen in the skin. In addition, an apple extract is known to have effects of soothing and moisturizing the skin, and apples and apple juice are known to have skin exfoliation effects by containing malic acid, tartaric acid, and amylase enzyme.

Currently, various food and cosmetic compositions using apples have been developed. However, as there is increasing domestic and foreign demand for compositions capable of improving skin conditions by preventing or inhibiting photoaging, the development of novel compositions with better effects of preventing or inhibiting photoaging is required.

DISCLOSURE

Technical Problem

The present disclosure provides a fermented apple composition, and use thereof in the skin improvement and in the prevention or inhibition of skin photoaging.

Technical Solution

An object of the present disclosure is to provide a fermented apple composition having an effect of reducing or inhibiting UV-induced collagenase expression.

Another object of the present disclosure is to provide a food including the fermented apple composition of the present disclosure.

Still another object of the present disclosure is to provide a health functional food including the fermented apple composition of the present disclosure.

Still another object of the present disclosure is to provide a cosmetic composition including the fermented apple composition of the present disclosure.

Advantageous Effects

Since the fermented apple composition of the present disclosure has an effect of reducing or inhibiting UV-induced collagenase expression, it may be provided for use in improving the skin or in preventing or inhibiting skin photoaging.

BRIEF DESCRIPTION OF THE DRAWINGS

FIG. 1 shows results of examining expression levels of matrix metalloproteinase-1 (MMP-1) by treating UVB-irradiated HaCaT cells with different concentrations of a fermented apple composition or an apple concentrate. * indicates $p<0.05$, and ** indicates $p<0.01$.

DETAILED DESCRIPTION OF PREFERRED EMBODIMENTS

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below. Further, a number of papers and patent documents are referenced and cited throughout this specification. The disclosures of the cited papers and patent documents are incorporated herein by reference in their entirety to further clarify the level and scope of the subject matter to which the present disclosure pertains.

An aspect of the present disclosure provides a fermented apple composition having an effect of reducing or inhibiting UV-induced collagenase expression.

The fermented apple composition of the present disclosure may include purified water and an apple concentrate.

As used herein, the term "apple concentrate" means a liquid obtained by concentrating apples, and those prepared or those commercially available may be used without limitation. For example, the apple concentrate may be a 100% apple concentrate, but is not limited thereto. Further, the apple concentrate may have a sugar content of 60 brix or more, based on a refractometer, but is not limited thereto. In addition, the apple concentrate may have an acidity of 6% or less, but is not limited thereto.

In one embodiment, the apple concentrate in the fermented apple composition of the present disclosure may refer to a component included before fermentation. Specifically, in the fermented apple composition of the present disclosure, the apple concentrate may be included in a volume of 1% (v/v) to 50% (v/v), 1% (v/v) to 30% (v/v), 1% (v/v) to 25% (v/v), 5% (v/v) to 50% (v/v), 5% (v/v) to 30% (v/v), 5% (v/v) to 25% (v/v), 10% (v/v) to 50% (v/v), 10% (v/v) to 30% (v/v), 10% (v/v) to 25% (v/v), 15% (v/v) to 50% (v/v), 15% (v/v) to 30% (v/v) or 15% (v/v) to 25% (v/v) with respect to the total volume of the fermented apple composition.

As used herein, the term "fermented apple composition" refers to a fermentation product resulting from fermentation of the apple concentrate.

As used herein, the term "fermentation" commonly refers to a phenomenon or process in which microorganisms convert and accumulate metabolites by decomposing organic matter using their own enzymes.

As used herein, the term "fermentation product" may be comprehensively interpreted as including all of a material produced by fermentation of the present disclosure, a filtrate thereof, a dilution thereof, a concentrate thereof, a crude product thereof, or a purified product thereof, etc., but is not limited thereto.

Specifically, the fermentation product of the present disclosure may be an acetic acid fermentation product or vinegar. More specifically, the fermentation product of the present disclosure may be a yeast and acetic acid bacteria fermentation product. Much more specifically, the fermentation product of the present disclosure may be a fermentation product of acetic acid bacteria after yeast fermentation.

For example, the fermented apple composition of the present disclosure may be an apple acetic acid-fermented composition, an apple acetic acid fermentation product, or an apple vinegar, which is obtained by fermentation of apple with acetic acid bacteria. Further, the fermented apple composition of the present disclosure may be an apple yeast-fermented and acetic acid bacteria-fermented composition, which is obtained by fermentation of apple with yeast and acetic acid bacteria. Furthermore, the fermented apple composition of the present disclosure may be an acetic acid bacteria-fermented composition post-yeast fermentation of apple, which is obtained by fermentation of apple with acetic acid bacteria after fermentation of apple with yeast.

In the present disclosure, the fermented apple composition of the present disclosure may have an effect of inhibiting UV-caused collagen degradation.

The inhibiting of collagen degradation may be achieved by, for example, reducing or inhibiting expression of collagenase.

The collagenase of the present disclosure may be matrix metalloproteinase-1 (MMP-1), MMP-2, or MMP-9, and any collagenase may be included in the scope of the present disclosure, as long as it is known in the art. In one embodiment, the collagenase may be MMP-1.

When UV-irradiated cells are treated with the fermented apple composition of the present disclosure, the UV-induced collagenase expression may be reduced or inhibited, as compared to UV-irradiated cells without treatment with the fermented apple composition.

For example, the fermented apple composition may reduce or inhibit the UV-induced collagenase expression in the range consisting of one lower limit selected from 10% or more, 15% or more, 20% or more, 21% or more, 22% or more, 23% or more, 24% or more, 25% or more, 26% or more, 27% or more, 28% or more, 29% or more, and 29.1% or more, and/or one upper limit selected from 100% or less, 50% or less, 40% or less, and 35% or less, but is not limited thereto.

In the present disclosure, the fermented apple composition of the present disclosure may have an effect of improving the skin.

In the present disclosure, the fermented apple composition of the present disclosure may have an effect of preventing skin aging.

As used herein, the term "skin improvement" refers to improvement of skin conditions by an anti-aging effect on the skin. Alternatively, it may refer to improvement or enhancement of skin health conditions.

The aging may be photoaging. More specifically, the aging may be UV-induced skin aging.

The skin improvement or skin anti-aging may be achieved by, for example, inhibiting degradation of collagen, and/or reducing or inhibiting expression of collagenase, which is as described above.

In the present disclosure, the fermented apple composition of the present disclosure may have an effect of inhibiting UV-induced wrinkle formation.

The inhibiting of wrinkle formation may be achieved by, for example, inhibiting degradation of collagen, and/or reducing or inhibiting expression of collagenase, which is as described above.

Another aspect of the present disclosure provides a food including the fermented apple composition of the present disclosure.

The fermented apple composition is as described above.

In the present disclosure, the food of the present disclosure may have an effect of improving or enhancing skin health. The improvement or enhancement of skin health may be achieved by, for example, inhibiting degradation of collagen, and/or reducing or inhibiting expression of collagenase, which is as described in the "skin improvement" of the previous aspect.

Still another aspect of the present disclosure provides a health functional food including the fermented apple composition of the present disclosure.

The fermented apple composition is as described above.

In the present disclosure, the health functional food of the present disclosure may have an effect of improving or enhancing skin health. The improvement or enhancement of skin health may be achieved by, for example, inhibiting degradation of collagen, and/or reducing or inhibiting expression of collagenase, which is as described in the "skin improvement" of the previous aspect.

The "food" of the present disclosure may include all types of general foods, functional foods, nutritional supplements, health foods, food additives, etc.

The above type of food may be prepared into various forms according to common methods known in the art.

The food includes forms such as pills, powders, granules, infusions, tablets, capsules, powders or liquids, etc., and foods to which the composition of the present disclosure may be added may include, for example, various foods, such as rice, edible grain flour (edible grain powder), grain soup, rice bowl, noodles, rice soup, instant rice, seasoning, lunch box rice, dried cooked rice, bread, edible sugar, rice cake, bibimjang, sauce, spice, edible salt, seasoning, seasoning powders, processed, frozen, dried and cooked fruits and vegetables, jellies, jams, compotes, eggs, milk and other dairy products, edible oils and fats, coffee, cocoa and coffee substitutes, tapioca, grain flour and grain preparations, ramen, udon, noodles, noodle soup, cold noodles, porridge, soup, soup dishes, instant foods, frozen foods, instant foods, retort foods, other beverages, chewing gum, tea, vitamin complex, health supplements, etc., but is not limited thereto.

As ingredients that may be included in the food of the present disclosure, various herbal extracts, food auxiliary additives, or natural carbohydrates may be included as additional ingredients, like in general foods. Further, the food auxiliary additives may include food auxiliary additives common in the art, for example, flavoring agents, savory agents, coloring agents, fillers, stabilizers, etc.

Examples of the natural carbohydrates include monosaccharides, for example, glucose, fructose, etc.; disaccharides, for example, maltose, sucrose, etc.; and polysaccharides, for example, common sugars such as dextrins, cyclodextrins, etc., and sugar alcohols such as xylitol, sorbitol, erythritol, etc. In addition to those described above, natural flavors (e.g., rebaudioside A, glycyrrhizin, etc.) and synthetic flavors (saccharin, aspartame, etc.) may be advantageously used as flavoring agents. In addition, common food additives used for the purpose of supplementing taste and nutrition, for example, nucleic acids, amino acids, organic acids, etc., may be added.

In addition to those described above, the food of the present disclosure may include various nutrients, vitamins, minerals (electrolytes), flavors such as synthetic flavors and natural flavors, etc., coloring agents and fillers (cheese, chocolate, etc.), pectic acid or salts thereof, alginic acid and salts thereof, organic acids, protective colloidal thickeners, pH adjusters, stabilizers, preservatives, glycerin, alcohols, carbonation agents used in carbonated drinks, etc. In addition, the food may include fruit flesh for the preparation of natural fruit juices, fruit juice beverages and vegetable beverages. These components may be used independently or in combination.

The food of the present disclosure may be prepared by a method commonly used in the art, and may be prepared by adding raw materials and ingredients commonly added in the art during the preparation. In addition, the formulation of the food may also be prepared without limitation as long as the formulation is recognized as a food.

Further, when the food of the present disclosure is used as a health functional food, the food of the present disclosure may be prepared in various types of formulations, and unlike general medicines, since the food is used as a raw material, there are advantages of being free from side effects that may occur when taken for a long period of time, and of being highly portable, and therefore, the food of the present disclosure may be ingested as a supplement.

Meanwhile, the food of the present disclosure may also include flavoring agents, savory agents, coloring agents, fillers, stabilizers, and flavors which may also be classified as food additives.

As used herein, the term 'flavor' may be a material added to enhance the flavor of food. The flavor may be a material that allows foods to have excellent seasoning property.

The flavor may be divided according to taste components. In other words, according to the taste, the flavor may be divided into neutral flavor, beef flavor, chicken flavor, pork flavor, kokumi flavor, etc.

The 'kokumi flavor' means a flavor which releases the flavor of kokumi, and the 'kokumi' is a Japanese word, and may also be expressed as 'mouthfulness', 'continuity', 'thickness', and 'heartiness' in English, and expressed as 'rich taste', 'thick taste', 'mouth-filling taste', 'dense taste', 'sticky taste', etc. in Korean. The 'neutral flavor' refers to a flavor that maximizes 'umami' and minimizes other flavors to produce a mild and clean flavor. For example, oils such as canola oil or grapeseed oil among oils may be acknowledged as having a neutral flavor. The term 'seasoning property' may mean to have a sour, sweet, salty, bitter, or umami taste, but is not limited thereto.

The food of the present disclosure may be a CJ CheilJedang Co., Ltd.'s apple vinegar or fruit fermented cider vinegar, for example, Petitzel Micho® or Micho® product, but is not limited thereto. The food of the present disclosure may include the fermented apple composition of the present disclosure at a concentration of 1% (v/v) to 50% (v/v), 1% (v/v) to 30% (v/v), 5% (v/v) to 50% (v/v), 5% (v/v) to 30% (v/v) or 10% (v/v) to 30% (v/v) with respect to the total volume of the food, but is not limited thereto.

Still another aspect of the present disclosure provides a cosmetic composition including the fermented apple composition of the present disclosure.

The fermented apple composition is as described above.

In the present disclosure, the cosmetic composition of the present disclosure may have an effect of relaxing or improving skin wrinkles. The relaxation or improvement of wrinkles may be achieved by, for example, inhibiting degradation of collagen, and/or reducing or inhibiting expression of collagenase, which is as described in the "inhibition of wrinkle formation" of the previous aspect.

In the present disclosure, the cosmetic composition of the present disclosure may have an effect of improving the skin or preventing skin aging. The improvement of the skin or the prevention of skin aging may be achieved by, for example, inhibiting degradation of collagen, and/or reducing or inhibiting expression of collagenase, which is as described in the previous aspect.

The "cosmetic composition" of the present disclosure may be prepared into a formulation selected from the group consisting of solutions, ointments for external use, creams, foams, nutrient lotions, softening lotions, packs, softening water, emulsions, makeup bases, essences, soaps, liquid cleansers, bath preparations, sunscreen creams, sun oil, suspensions, emulsions, pastes, gels, lotions, powders, soaps, surfactant-containing cleansers, oils, powder foundations, emulsion foundations, wax foundations, patches and sprays, but is not limited thereto.

The cosmetic composition may further include one or more cosmetically acceptable carriers which are blended in general skin cosmetics, and as common ingredients, for example, oil, water, surfactants, moisturizers, lower alcohols, thickeners, chelating agents, pigments, preservatives, flavoring agents, etc. may be appropriately blended, but are not limited thereto. The cosmetically acceptable carrier included in the cosmetic composition of the present disclosure may be appropriately selected by those skilled in the art according to the formulation of the cosmetic composition.

The cosmetic composition of the present disclosure may include the fermented apple composition of the present disclosure at a concentration of 0.001% (v/v) to 2% (v/v), 0.005% (v/v) to 1.9% (v/v), 0.02% (v/v) to 1.8% (v/v), 0.025% (v/v) to 1.75% (v/v), 0.03% (v/v) to 1.7% (v/v), 0.035% (v/v) to 1.65% (v/v), 0.04% (v/v) to 1.6% (v/v), 0.045% (v/v) to 1.55% (v/v), or 0.05% (v/v) to 1.5% (v/v) with respect to the total volume of the cosmetic composition. In one embodiment, the cosmetic composition may include the fermented apple composition of the present disclosure at a concentration of 0.05% (v/v) to 1.5% (v/v) with respect to the total volume of the cosmetic composition, but is not limited thereto.

Still another aspect of the present disclosure provides a method of reducing or inhibiting UV-induced collagenase expression, the method including the step of administering the fermented apple composition of the present disclosure.

The collagenase may be, but is not limited to, MMP-1, which is as described above.

The fermented apple composition may reduce or inhibit the UV-induced collagenase expression by 10% or more when UV-irradiated cells are treated therewith, as compared to UV-irradiated cells without treatment with the fermented apple composition, but is not limited thereto. This is as described above.

Still another aspect of the present disclosure provides a method of improving the skin, the method including the step of administering the fermented apple composition of the present disclosure.

Still another aspect of the present disclosure provides a method of preventing skin aging, the method including the step of administering the fermented apple composition of the present disclosure.

The aging may be photoaging, but is not limited thereto. This is as described above.

Still another aspect of the present disclosure provides a method of preventing UV-induced wrinkle formation, the method including the step of administering the fermented apple composition of the present disclosure.

As used herein, the term "administering" means introducing the composition of the present disclosure to a subject, in which inflammatory cytokines are excessively expressed or enteritis is suspected, by any suitable method.

The pharmaceutical composition of the present disclosure is not particularly limited, as long as the subject is a subject for the purpose of reducing or inhibiting the UV-induced collagenase expression, or improving the skin, preventing skin aging, or inhibiting UV-induced wrinkle formation, and the composition is applicable to any subject. For example, the composition may be applied to any subject of non-human animals such as monkeys, dogs, cats, rabbits, guinea pigs, rats, mice, cows, sheep, pigs, goats, etc., birds and fish, etc.

The composition of the present disclosure may be administered in an amount effective for reducing or inhibiting the UV-induced collagenase expression, or administered in an amount effective for improving the skin, administered in an amount effective for preventing skin aging, or administered in an amount effective for inhibiting UV-induced wrinkle formation. The preferred dosage of the composition of the present disclosure may vary depending on the subject's conditions and body weight, severity of the disease, the type of drug, the route of administration and the duration, but may be appropriately selected by those skilled in the art.

In addition, the composition of the present disclosure may be administered through various oral or parenteral routes as long as it is able to reach a target tissue. For example, it may be administered orally, parenterally, subcutaneously, intraperitoneally, intrapulmonary, intranasally, rectally or intravenously, intramuscularly, subcutaneously, intrauterine or intracerebral injection, and for local treatment, if necessary, by any suitable method including intralesional administration, but is not limited thereto.

In one embodiment, the fermented apple composition may be administered in the form of a food composition including the same. In this regard, the administration may be oral administration.

In another embodiment, the fermented apple composition may be administered in the form of a health functional food composition including the same. In this regard, the administration may be oral administration.

Still another aspect of the present disclosure provides a method of reducing or inhibiting UV-induced collagenase expression, the method including the step of applying the fermented apple composition of the present disclosure to the skin.

Still another aspect of the present disclosure provides a method of improving the skin, the method including the step of applying the fermented apple composition of the present disclosure to the skin.

Still another aspect of the present disclosure provides a method of preventing skin aging, the method including the step of applying the fermented apple composition of the present disclosure to the skin.

Still another aspect of the present disclosure provides a method of inhibiting UV-induced wrinkle formation, the method including the step of applying the fermented apple composition of the present disclosure to the skin.

As used herein, the term "applying" means bringing the composition of the present disclosure into contact with a subject's skin by any suitable method, and includes all of the actions by which the corresponding composition is intended to be absorbed into the skin, but is not limited thereto.

In one embodiment, the fermented apple composition may be applied to the skin in the form of a cosmetic composition including the same.

Still another aspect of the present disclosure provides use of the fermented apple composition of the present disclosure in reducing or inhibiting the UV-induced collagenase expression.

The collagenase may be MMP-1, but is not limited thereto. This is as described above.

The fermented apple composition may reduce or inhibit the UV-induced collagenase expression by 10% or more when UV-irradiated cells are treated therewith, as compared to UV-irradiated cells without treatment with the fermented apple composition, but is not limited thereto. This is as described above.

Still another aspect of the present disclosure provides use of the fermented apple composition of the present disclosure in improving the skin.

Still another aspect of the present disclosure provides use of the fermented apple composition of the present disclosure in preventing skin aging.

The aging may be photoaging, but is not limited thereto. This is as described above.

Still another aspect of the present disclosure provides use of the fermented apple composition of the present disclosure in inhibiting UV-induced wrinkle formation.

Still another aspect of the present disclosure provides use of the food including the fermented apple composition of the present disclosure in improving or enhancing skin health.

Still another aspect of the present disclosure provides use of the health functional food including the fermented apple composition of the present disclosure in improving or enhancing skin health.

Still another aspect of the present disclosure provides use of the cosmetic composition including the fermented apple composition of the present disclosure in relaxing or improving skin wrinkles.

The terms used herein are as described in the previous aspects.

MODE FOR CARRYING OUT THE INVENTION

Hereinafter, the present disclosure will be described in more detail with reference to exemplary embodiments. However, the following exemplary embodiments are merely preferred embodiments for illustrating the present disclosure, and therefore, are not intended to limit the scope of the present disclosure thereto. On the other hand, technical details not described in this specification may be sufficiently understood and easily implemented by those skilled in the art or similar art.

Preparation Example 1: Preparation of Fermented Apple Composition

An apple concentrate was a commercially available product with 100% concentration of apples. An apple concentrate made in China, of which a sugar content was 60 brix or more, based on a refractometer, and an acidity was 6% or less, was diluted with distilled water 4 times (w/w) to prepare the apple concentrate at about 20 brix.

As a fermented apple composition, a commercially available apple cider vinegar (a yeast and acetic acid bacteria-fermented product, containing purified water and 20.86% of apple concentrate and having acidity of 6% to 8%; healthy fermented apple cider vinegar from CJ CheilJedang Co., Ltd.) was used.

To remove microorganisms from the fermented apple composition and the apple concentrate, filtration was performed using a 0.2 um filter.

Example 1: Evaluation of Photoaging-Inhibitory Ability In Vitro

The photoaging-inhibitory ability of the fermented apple composition and the apple concentrate was analyzed using HaCaT cells, in which overexpression of a collagenase. MMP-1 (Matrix metalloproteinases-1) was induced by UVB irradiation.

Specifically, the HaCaT cell line (Korea Cell Line Bank) was cultured in an FBS-contained DMEM medium (Gibco, USA) under conditions of 37° C. and 5% $CO_2$ to obtain cells at passages 8 to 12. The obtained HaCaT cells were diluted at a density of $0.7 \times 10^5$ cells/well using FBS-contained DMEM, and seeded into a 24-well plate, and cultured for 2 days under conditions of 37° C. and 5% $CO_2$. The medium was replaced by FBS-free DMEM to give the cells starvation conditions, followed by incubation for 1 day (FIG. 1, indicated by NC). Then, the cells were washed twice with Phosphate-Buffered Saline (PBS, Gibco), and then 500 mL of PBS was added to the well, and 20 mJ/cm² of UVB was irradiated to induce MMP-1 overexpression, followed by additional washing with PBS twice (FIG. 1, indicated by CON). As an experimental group, the fermented apple composition and the apple concentrate of Preparation Example 1 were diluted at a concentration of 1% (v/v) with FBS-free DMEM, respectively and then treated to the cells (CON), followed by incubation for 1 day. After culturing, the supernatant was taken and centrifuged at 4° C. at 13,000 rpm for 3 minutes to obtain only the supernatant excluding cells. Thereafter, to remove residual cells in the supernatant, filtration was performed using a 0.2 um filter.

The concentration of MMP-1 was measured by analyzing the obtained supernatant by an ELISA assay.

In detail, the ELISA assay was performed according to the instructions of the manufacturer of a Human Total MMP-1 DuoSet ELISA (R&D systems) as follows. First, a capture antibody was attached to each well of a 96-well plate overnight. After washing the plate three times with a washing buffer, a reagent diluent was treated for 1 hour. Then, after additional washing three times with the washing buffer, the supernatant of each experimental group and control group (NC, CON) and standard solution were put into each well and incubated for 2 hours. After washing them, a detection antibody was added and attached for 2 hours. After additional washing, each well was treated with streptavidin-HRP B for 20 minutes. The reaction was stopped by treating with a reaction stopping solution, and then absorbance was measured at 450 nm, and the MMP-1 concentration was calculated using a 4-parameter logistic.

As a result, both the fermented apple composition and the apple concentrate significantly reduced MMP-1 at concentrations of 1% (v/v), and the fermented apple composition (29.1%) showed the higher MMP-1 reduction rate than the apple concentrate (11.5%) (FIG. 1 and Table 1).

Accordingly, it was confirmed that both the fermented apple composition and the apple concentrate exhibited the photoaging-inhibitory ability, and in particular, the fermented apple composition had the excellent photoaging-inhibitory ability, as compared to the apple concentrate.

TABLE 1

| Treatment group (treatment concentration 1% (v/v)) | MMP-1 concentration (pg/mL) |
|---|---|
| NC | 3052.0 |
| CON | 6002.6 |
| Apple concentrate | 5311.9 |
| Fermented apple composition | 4256.4 |

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the present disclosure is defined by the appended claims rather than by the description preceding them, and therefore all changes and modifications that fall within metes and bounds of the claims, or equivalents of such metes and bounds are therefore intended to be embraced by the claims.

The invention claimed is:

1. A fermented apple composition having an effect of reducing or inhibiting UV-induced collagenase expression, wherein the fermented apple composition consists of a fermented product produced by fermentation of an apple concentrate and purified water with yeast and acetic acid bacteria.

2. The fermented apple composition of claim 1, wherein the collagenase is MMP-1.

3. The fermented apple composition of claim 1, wherein the fermented apple composition has an effect of improving the skin.

4. The fermented apple composition of claim 1, wherein the fermented apple composition has an effect of preventing skin aging.

5. The fermented apple composition of claim 4, wherein the aging is photoaging.

6. The fermented apple composition of claim 1, wherein the fermented apple composition has an effect of inhibiting UV-induced collagen degradation.

7. The fermented apple composition of claim 1, wherein the fermented apple composition reduces or inhibits the UV-induced collagenase expression by 10% or more when UV-irradiated cells are treated therewith, as compared to UV-irradiated cells without treatment with the fermented apple composition.

8. The fermented apple composition of claim 1, wherein the fermented apple composition has an effect of inhibiting UV-induced wrinkle formation.

9. A food comprising the fermented apple composition of claim 1.

10. The food of claim 9, wherein the food is for improving or enhancing skin health.

11. A health functional food comprising the fermented apple composition of claim 1.

12. The health functional food of claim 11, wherein the health functional food is for improving or enhancing skin health.

13. A cosmetic composition comprising the fermented apple composition of claim 1.

14. The cosmetic composition of claim 13, wherein the cosmetic composition is for relaxing or improving skin wrinkles.

* * * * *